United States Patent [19]

Kieran et al.

[11] Patent Number: 5,286,749
[45] Date of Patent: Feb. 15, 1994

[54] CONTROL OF SHEEP ECTOPARASITES

[75] Inventors: Peter J. Kieran, Beecroft; Robert B. Townsend, Waitara, both of Australia

[73] Assignee: Pitman-Moore Inc., Lake Forest, Ill.

[21] Appl. No.: 597,110

[22] Filed: Oct. 12, 1990

Related U.S. Application Data

[63] Continuation of Ser. No. 355,087, May 18, 1989, abandoned, which is a continuation of Ser. No. 935,113, Nov. 26, 1986, abandoned, which is a continuation of Ser. No. 640,029, Aug. 10, 1984, abandoned, which is a continuation of Ser. No. 323,117, Nov. 20, 1981, abandoned.

[30] Foreign Application Priority Data

Nov. 21, 1980 [AU] Australia .............................. PE 6592

[51] Int. Cl.$^5$ .................... A01N 53/00; A61K 31/215
[52] U.S. Cl. ..................................... 514/531; 514/521
[58] Field of Search ................................ 514/521, 531

[56] References Cited

U.S. PATENT DOCUMENTS

| | | |
|---|---|---|
| 3,235,451 | 2/1966 | Odeneal . |
| 4,020,181 | 4/1977 | Blackman et al. . |
| 4,100,297 | 7/1978 | Grandadam et al. . |
| 4,171,355 | 10/1979 | Stubbs et al. . |
| 4,218,469 | 8/1980 | Fuchs et al. . |
| 4,341,760 | 7/1982 | Matthewson .................. 424/304 |

FOREIGN PATENT DOCUMENTS

| | | |
|---|---|---|
| 494198 | 6/1974 | Australia . |
| 0000345B1 | 1/1979 | European Pat. Off. . |
| 191772 | 3/1981 | New Zealand . |
| 186082 | 10/1981 | New Zealand . |
| 193877 | 3/1982 | New Zealand . |
| 195796 | 8/1984 | New Zealand . |
| 197891 | 12/1984 | New Zealand . |
| 199904 | 5/1985 | New Zealand . |
| 2965475A | of 0000 | United Kingdom . |
| 1488906 | 11/1974 | United Kingdom . |
| 1413491 | 11/1975 | United Kingdom . |
| 1511646 | 5/1978 | United Kingdom . |
| 1516113 | 6/1978 | United Kingdom . |
| 1534527 | 12/1978 | United Kingdom . |
| 2002635A | 2/1979 | United Kingdom . |
| 2015877A | 9/1979 | United Kingdom . |
| 2024625A | 1/1980 | United Kingdom . |
| 2029226A | 3/1980 | United Kingdom . |
| 2031729A | 4/1980 | United Kingdom . |
| 1580251 | 11/1980 | United Kingdom . |
| 1591105 | 6/1981 | United Kingdom . |
| 1591106 | 6/1981 | United Kingdom . |

OTHER PUBLICATIONS

Stomoxin MO, (Permethrin 25:75), Residual Insecticide Spray.
The External Parasites of Sheep and Their Control: Decacide.
BASH, Technical Manual, New Zealand Trials (21 pages) Decacide (1980).
Off Shears Backline Sheep Treatment, Technical Bulletin: Decacide.
Farm Equipment News, Issue 39, Feb. 19, 1979.
Mayfield, et al., J. Text. Inst., 1979, No. 2, pp. 53-61, 6-A Comparison of New Synthetic Pyrethroids for the Industrial Insectproofing of Wool.
18 Teams in Maranoa Weather Trial, Sep. 25, 1980.
Farm Equipment News, Off-Shears Backline Lice Treatment, Decacide, Jan. 19, 1981.
Letters to the Editor, New Zealand Veterinary Journal, vol. 20(9), Sep. 1972, p. 167.
New Zealand Veterinary Journal, vol. 25, pp. 403-404 (1977).
C. A. Hall, Australian Veterinary Journal, vol. 54, Oct. 1978, The Efficiency of Cypermethrin (NRDC 149) For the Treatment and Eradication of the Sheep Lousee Damalinia Ovis.
M. Elliot, et al., Ann. Rev. Entomol. 23:443-469 (1978), The Future of Pyrethroids in Insect Control.

(List continued on next page.)

Primary Examiner—Sam Rosen
Attorney, Agent, or Firm—Donald Brown

[57] ABSTRACT

A topical liquid formulation for treating lice or head infection is disclosed. The formulation contains active ingredients such as deltamethrin or permethrin in a lower alkyl ether of glycol.

4 Claims, No Drawings

OTHER PUBLICATIONS

A. N. Sinclair, et al., Australian Veterinary Journal, vol. 41, Nov. 1965, pp. 341–346, Control of the External Parasites of Sheep by Application of Insecticides Solution to the Mid-Dorsal Zone.

W. M. Rogoff, et al., Journal of Economic Entomology, vol. 53, No. 5, pp. 814–817, Effectiveness of Ruelene Applied as Localized "Pour-On" and as Spray for Cattle Grub Control.

The Australian Veterinary Journal, Dec. 1957, pp. 330–331, Diseases of Livestock, Eighth Edition, Hungerford, et al., pp. 946–947, 763.

Jetting Sheep, B. C. Jefferies, The Journal of Agriculture, S. Australia, Aug. 1956, 1979 Farm Chemical Handbook.

A Manual of Australian Agriculture, R. L. Reid, pp. 323–332, Veterinary Prescribers Index 1979, First Edition, R. A. & R. J. Wailes, pp. 64–66.

Sinclair, The Veterinary Review, vol. 24, pp. 95–101, The Unusual Nature of Sheep Fleece in Relation to Applied Insecticide.

The Application of Insecticides to Sheep and Cattle in Temperate Zones, Aug. 1970.

D. K. O'Neil, Investigation of Sheep Dips, Australian Veterinary Journal, vol. 44 Aug. 1968.

Sinclair, et al., Australian Veterinary Journal, vol. 41, Nov. 1965, Control of External Parasites of Sheep by Application of Insecticide Solution.

Sinclair, et al., Australian Veterinary Journal, vol. 40, Feb. 1964, Field Trails on Three Methods of Applying Diazinon to Sheep for Control of Blowfly Strike.

Sinclair, et al., Australian Veterinary Journal, vol. 39, Mar. 1963, Surface Spraying and Dusting as Means of Controlling External Parasites of Sheep.

The Australian Veterinary Journal, Jun. 1959, Surface Spraying and Dusting to Control Ectoparasites of Sheep, pp. 293–296.

Onderstepoort Journal of Veterinary Research, vol. 27, Jan. 1956. The Protection of Sheep Against Blowfly Strike. O. G. H. Fiedler, et al.

Onderstepoort Journal of Veterinary Research, vol. 26, No. 3, Jun. 1954, The Protection of Sheep Against Blowfly Strike (III) O. G. H. Fiedler, et al.

Onderstepoort Journal of Veterinary Research, vol. 26, No. 1, May 1953, The Protection of Sheep Against Blowfly Strike (I) R. Du Toit, et al.

Australian Veterinary Journal, vol. 54, Oct. 1978, C. A. Hall, The Efficiency of Cypermethrin (NRDC 149) For the Treatment and Eradication of Sheep Louse.

Trends in Veterinary Pharmacology and Toxicology, pp. 242–260, Joep Van Den Bercke.

50931/79, William Val Miller, Australian Specification "Animal Ear Tags, Their Manufacture and Their Use".

44794/79, Patrick George Feakins, Australian Specification, "Animal Ear Tags, Their Manufacture and Their Use".

Sheperd's Guide: A practical Treatise, James Hogg.

Pesticide Research Report, 1979.

Proceedings of the Entomological Society of Ontario, The Behaviour and Nutritional Requirements of Adults of Lucilla Cuprina-Possibilities for Modification L. Barton, pp. 45, 53.

1 page, MAF, 1976/77, p. 156.

Elliott, Science, Zurich, 1978, pp. 165–195, IIA—Structure-Activity Correlations in Recent Classes of Insecticides.

Chemicals for Crop Protection and Pest Control, Chapter 8, Pesticides of Natural Origin and Synthetic Pyrethroids, pp. 69–78.

Proceedings of the Entomological Society of Ontario, vol. 110, 1979, pp. 28–34.

Page 39, New Zealand Veterinary Journal, 1980.

J. Agric. Food Chem., vol. 27, No. 2, 1979, pp. 331–336, Mothproofing Wool and Wool Blends with Permethrin.

CONTROL OF SHEEP ECTOPARASITES

This application is a continuation of application Ser. No. 07/355,087, filed May 18, 1989 (now abandoned), which is a continuation of application Ser. No. 06/935,113, filed Nov. 26, 1986 (now abandoned), which is a continuation of application Ser. No. 06/640,029, filed Aug. 10, 1984 (now abandoned), which is a continuation of application Ser. No. 06/323,117, filed Nov. 20, 1981 (now abandoned).

The present invention relates to a method of controlling sheep ectoparasites including keds, lice, flies, mites and ticks. The invention has special application to the control of the sheep-biting louse (*Damalinia ovis*) and keds (*Melophagus ovinus*) particularly on merino sheep.

Traditionally, sheep have been treated for the control of ectoparasites by dipping or spraying the whole external surface of the sheep. However, this is an inconvenient and time-consuming operation. Attempts have been made to treat infested sheep, particularly lice-infested sheep, with a large variety of known insecticides by various more convenient routes, including pour-on treatments, subcutaneous injection, and by oral dosage. Hitherto, none of the treatments had any significant effect on the control of the lice populations. In particular, merino sheep which have very dense wool have not responded to such treatments.

The present invention is based on the unexpected discovery that localised applications of pyrethroids are surprisingly effective in controlling and eradicating lice, keds, blow flies and other ectoparasites. It is particularly surprising that such localised application is effective even on long-woolled merino sheep.

Thus, the present invention provides a method of controlling sheep ectoparasites which comprises the application onto a localised region of the skin or fleece of a sheep of a pyrethroid of the formula

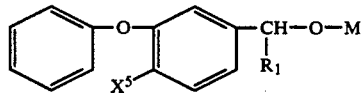

wherein
M is

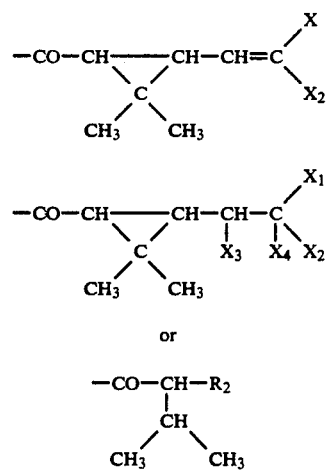

and wherein $X_1$ to $X_4$ are independently selected from halo, $C_1$-$C_4$ alkyl, halogen-substituted $C_1$-$C_4$ alkyl, and halogen-substituted phenyl;

$X_5$ —H or halo;

$R_1$ is —H or cyano; and $R_2$ is halogen-substituted phenyl.

By "localised application" is meant that the pyrethroid is only applied to a minor portion of the skin or fleece of the sheep, generally as a line or spot on the sheep's back. It has been surprisingly discovered that, notwithstanding the presence of a sometimes dense coating of wool, the pyrethroid appears to act over the entire surface of the sheep. It is believed as a hypothesis that the pyrethroid is transmitted over the surface of the sheep by diffusion through the wool grease.

The pyrethroid is generally applied as a liquid formulation, a paste or as a solid powder. Surprisingly, it has been found that it is not necessary that the pyrethroid be dissolved to be effective.

The localised application is preferably carried out as a pour-on treatment by pouring a liquid formulation comprising the pyrethroid along the back of the sheep (i.e. a so-called "backline" application). Surprisingly, it is not necessary to totally immerse the sheep in the formulation so that the treatment of large numbers of sheep is facilitated.

Alternatively, the application may be carried out by means of a localised spray or aerosol, usually along the sheep's back as it passes through a sheep race. The aerosol might comprise the pyrethroid dissolved in a liquid carbon dioxide propellant.

Without wishing to be limited by any theoretical mode of action, it is believed that the pyrethroid acts superficially and is not dermally and systemically absorbed. It is therefore surprising that protection over the entire sheep is attainable from a localised application.

The pyrethroid is preferably selected from the group of light stable pyrethroids. Deltamethrin (also known as decamethrin) is preferred and is a solid under normal conditions. Suitable pyrethroids are disclosed in Tables I to III.

TABLE I $$M = -CO-CH\underset{\underset{CH_3}{\diagup}\overset{C}{\diagdown}CH_3}{-----}CH-CH=C\overset{X_1}{\underset{X_2}{\diagdown}}$$

| No. | $X_1$ | $X_2$ | $X_3$ | $X_4$ | $X_5$ | $R_1$ | trivial name |
|-----|-------|-------|-------|-------|-------|-------|--------------|
| 1 | Cl | Cl | — | — | H | H | permethrin |
| 2 | CH$_3$ | CH$_3$ | — | — | H | H | phenothrin |
| 3 | Br | Br | — | — | H | CN | deltamethrin |
| 4 | Cl | Cl | — | — | H | CN | cypermethrin |
| 5 | Cl | CF$_3$ | — | — | H | CN | cyhalothrin |
| 6 | Cl | ⟨phenyl⟩-Cl | | — | — | F | CN | flumethrin |
| 7 | Cl | Cl | — | — | F | CN | cyfluthrin |
| 8 | CH$_3$ | CH$_3$ | — | — | H | CN | cyphenothrin |

TABLE II

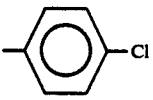

| No. | $X_1$ | $X_2$ | $X_3$ | $X_4$ | $X_5$ | $R_1$ | trivial name |
|---|---|---|---|---|---|---|---|
| 9 | Br | Br | Br | Br | H | CN | tralomethrin |
| 10 | Cl | Cl | Br | Br | H | CN | tralocythrin |

TABLE III $$M = -CO-CH-R_2$$
$$\quad\quad\quad\;|$$
$$\quad\quad\quad CH$$
$$\quad\quad\;/\quad\backslash$$
$$\;\;CH_3\quad CH_3$$

| No. | $R_2$ | $X_5$ | $R_1$ | trivial name |
|---|---|---|---|---|
| 11 | 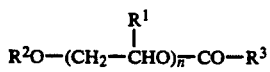 | H | CN | fenvalerate |

It is a particular advantage of the present method that only small volumes of pyrethroid o pyrethroid-containing formula need to be applied. Depending on the size of the sheep, the volume applied will generally lie in the range 2 to 15 ml per sheep. For convenience, the pyrethroid will generally be applied in a liquid formulation.

Depending on the efficacy of the particular pyrethroid employed, the formulation generally contains from 0.1 to 500, preferably 1 to 250 mg/ml of the pyrethroid. Moreover, the pyrethroid is preferably applied to the sheep in an application of from 1 to 500, preferably 1.5 to 250 mg/kg body weight.

The formulation may be applied to full-woolled or sheared sheep. However, higher doses are required for full-woolled sheep.

The pyrethroid is preferably applied in the form of a pour-on formulation. The formulation may comprise one or more organic solvents, such as xylene, toluene, cyclohexanone, and a glycol.

One preferred solvent system comprises 30-70 wt % xylene, 20-40 wt % cyclohexanone and 5-25 wt % vegetable oil.

Suitable glycols include ethylene glycol and propylene glycol, polyethylene glycols and polypropylene glycols, ethylene glycol - propylene glycol copolymers, and alkyl ethers and alkyl ether esters of the general formula:

$$R^2O-(CH_2-CHO)_n-CO-R^3$$
$$\quad\quad\quad\quad\quad\;|$$
$$\quad\quad\quad\quad\;\;R^1$$

where
$R^1 = C_1$ alkyl or hydrogen,
$R^2 = C_1-C_5$ alkyl, hydrogen or $-CO-R^3$,
$R^3 = C_1-C_{12}$ alkyl,
and n = 1-40.

Diethylene glycol mono-n-butyl ether has been found to be particularly useful. It has been found to have minimal adverse effect on the skin in terms of a mild epidermal shedding seen with other solvents in some sheep.

Alternatively, the formulation may be an aqueous formulation containing the pyrethroid in the form of a suspension or emulsion and comprising suitable surfactants to stabilise the suspension or emulsion, and prevent undue run-off from the back of the sheep. Thus, it has been surprisingly found that the pyrethroid is effective even when in the undissolved state.

Paraffin oils, vegetable oils, e.g. corn oil, peanut oil, castor oil, olive oil, can be added as viscosity modifiers and co-solvents.

Alkylamides and esters of fatty acids are useful formulation adjuncts e.g. n-butyl oleate, N,N-dimethyl oleamide and isopropyl myristate (IPM).

It has been found that the inclusion of an antioxidant such as 2,6-ditert-butyl-4-cresol (BHT) or 2-tert-butyl-4-methoxyphenol (BHA) has a useful stabilising effect on the active ingredients in formulations based on glycols, glycol ethers, glycol ether esters and cyclohexanone.

The present invention will now be illustrated with reference to comparative tests showing the lack of activity of a large number of conventional insecticides, and with reference to specific examples illustrating the present invention.

(I) COMPARATIVE TESTS

The effectiveness of a number of known insecticides in controlling sheep lice using pour-on formulations was assessed. A summary of the active agents and dose rates is given in Table 1.

TABLE 1

| Chemical | Pour-on (mg/kg) |
|---|---|
| chlorfenvinphos | 100 |
| maldison | 250 |
| carbaryl | 100 |
| dimethoate | 100 |
| dioxathion | 100 |
| ethion | 100 |
| fenitrothion | 100 |
| trichlorphon | 100 |
| famphur | 50, 100 |
| ronnel | 100 |
| crotoxyphos | 100 |
| bendiocarb | 100 |
| bromophos ethyl | 100 |
| dichlofenthion | 100 |
| crufomate | 100 |
| naled | 100 |

All the pour-on treatments were formulated in a solvent system containing xylene, cyclohexanone and corn oil.

A total of 18 groups of lice-infested merino sheep divided into control (1) and treatment groups (17) were selected and treated according to Table 1.

No pour-on treatment had any significant effect on existing lice burdens.

(II) TREATMENT ACCORDING TO THE PRESENT INVENTION

A variety of pyrethroids were evaluated in the control of lice and keds on merino sheep, when applied by a liquid pour-on formulation.

Test 1 (xylene-cyclohexanone-corn oil solvent)

Forty-eight merino sheep, half carrying full-wool and half carrying one month's wool, with significant louse infestations, were allocated equally into four groups of six animals.

Treatments, with formulations comprising a xylene (55 wt %), cyclohexanone (30 wt %), corn oil (15 wt %) solvent system were made as follows:

| Group 1 | deltamethrin | 10 mg/kg | 10 mg/ml formulation |
| Group 2 | deltamethrin | 50 mg/kg | 50 mg/ml formulation |
| Group 3 | permethrin | 100 mg/kg | 100 mg/ml formulation |
| Group 4 | permethrin | 250 mg/kg | 250 mg/ml formulation |

On full-woolled sheep, partings were made along the backline to place the formulation at skin level. After treatment the various groups, each with three full-woolled and three short-woolled sheep, were held in separate pens, remote from each other.

Post-treatment lice examinations were made at 1, 3 and 7 weeks, to assess the effects of the various treatments on the louse populations.

At seven weeks, groups 1 and 2 were run with a mob of fifteen infestor sheep, carrying considerable lice infestations, to gauge the persistence of deltamethrin. Further examinations were made at 9 weeks but subsequent examinations were prevented by wet weather.

Results

The results of the pre-treatment and post-treatment lice examinations are shown in Table 2 and are outlined below.

GROUP 1
deltamethrin (10 mg/kg)
full wool
Infestations fell rapidly to extremely low levels and persisted at these low levels throughout the trial.
short wool
One light infestation was eradicated by Week 1. Moderate to heavy infestations were eradicated by Week 7.
GROUP 2
deltamethrin (50 mg/kg)
full wool
At one week, two newly emerged lice were found in matted wool on one animal, only after an exhaustive search. No lice were seen on the other two animals. At Week 3 an exhaustive search of each animal revealed one or two newly emerged lice. No lice were found at Week 7 or at Week 9, after a fourteen-day challenge period.
short wool
No lice were seen at any examination after treatment.
GROUP 3
permethrin (100 mg/kg)
full wool
Infestations were markedly reduced but were maintained at low levels throughout the trial.
short wool
Infestations were reduced to extremely low levels but lice were still present at Week 7.
GROUP 4
permethrin (250 mg/kg)
full wool
Infestations were greatly reduced on two out of three sheep but persisted at low levels until Week 7. Lice were eradicated on the third animal by Week 7.
short wool
Light infestations were drastically reduced at Week 1 and eradicated at Week 3.

In the following tables, the numbers represent the total number of lice detected in twenty partings of the wool of the sheep, and

| L = light infestation | 0 = no lice present |
| M = moderate infestation | + = lice present. |
| H = high infestation | |

TABLE 2

(First Three Sheep per Group Carrying Full-Wool, Second Three Carrying One Month's Wool)

| Group | | Sheep No. | Pre-Treatment | Week 1 | Week 3 | Week 7 | Week 9 | Comments |
|---|---|---|---|---|---|---|---|---|
| GROUP 1 | B | 34 | H | 13/20 | 24/20 | 16/20 | 2/20 | *One heavy |
| deltamethrin | B | 882 | H | L-M | L-M | 2/20* | 8/20* | patch found |
| (10 mg/kg) | O | 800 | L | 0 | 0 | 0 | 0 | in neck fold |
| | B | 28 | M-H | 14/20 | 0 | 0 | 0 | |
| | Y | 749 | M-H | 3/20 | 1/20 | 0 | 0 | |
| GROUP 2 | B | 883 | M-H | 0 | 5/20 | 0 | 0 | **Found in |
| deltamethrin | G | 790 | H | 2/20** | 1/20 | 0 | 0 | matted wool |
| (50 mg/kg) | Y | 840 | M-H | 0 | 2/20 | 0 | 0 | |
| | B | 44 | M-H | 0 | 0 | 0 | 0 | |
| | Y | 830 | L-M | 0 | 0 | 0 | 0 | |
| | Y | 738 | M | 0 | 0 | 0 | 0 | |
| GROUP 3 | B | 50 | H | L | L | L | | |
| permethrin | Y | 835 | H | M | M-H | M-H | | |
| (100 mg/kg) | Y | 833 | H | L | L | 19/20 | | |
| | B | 27 | M-H | 20/20 | 9/20 | 24/20 | | |
| | B | 49 | M | 17/20 | 6/20 | 11/20 | | |
| | Y | 744 | L-M | 7/20 | 3/20 | 4/20 | | |
| GROUP 4 | B | 887 | H | 12/20 | 7/20 | 3/20 | | |
| permethrin | B | 38 | L-M | 7/20 | 0 | 0 | | |
| | B | 42 | H | L-M | L-M | L | | |
| | B | 35 | L | 1/20 | 0 | 0 | | |
| | B | 29 | L | 1/20 | 0 | 0 | | |
| | Y | 991 | L | 1/20 | 0 | 0 | | |
| CONTROLS | | 47 | L-M | M-H | M | L | L | |
| | | 877 | H | H | H | H | H | |
| | | 742 | H | H | H | M-H | M-H | |
| | | 754 | L | L-M | L-M | L | L-M | |

TABLE 2-continued (First Three Sheep per Group Carrying Full-Wool, Second Three Carrying One Month's Wool)

| Group | Sheep No. | Pre-Treatment | Week 1 | Week 3 | Week 7 | Week 9 | Comments |
|---|---|---|---|---|---|---|---|
| | 37 | M | M | L | L | L-M | |
| | 736 | L-M | M | L-M | died | | |

Test 2

The results of the evaluation of deltamethrin on recently sheared merino sheep using xylene and DGBE-based solvent systems are given in Tables 3 and 4. The results of the untreated control group are given in Table 5.

The xylene-based solvent system is the same as that given in Test 1.

The DGBE-based solvent system had a composition as follows:

| | |
|---|---|
| diethylene glycol mono-n-butyl ether (DGBE) | 85 wt % |
| isopropyl myristate (IPM) | 15 wt % |
| 2,6-ditert-butyl-4-cresol (BHT) | 2.5 g/l. |

TABLE 3

Xylene-Based Solvent*

| Deltamethrin (g/l) | Group | Sheep No. | Body-weight (kg) | Dose (ml) | Post-Treatment Inspections week 3 | week 6 | Challenge Inspections (Group 1 and Group 2) week 10 | week 12 | week 14 |
|---|---|---|---|---|---|---|---|---|---|
| 8.0 | GROUP 1 (a) | 51 | 50 | 6.3 | 0 | 0 | 0 | 0 | 1 |
| | 1 mg/kg | 90 | 46 | 5.8 | 0 | 0 | 0 | 0 | 2 |
| | 1 ml/8 kg | 106 | 44 | 5.5 | 0 | 0 | 0 | 0 | 0 |
| 4.0 | GROUP 1 (b) | 52 | 44 | 11.0 | 0 | 0 | 0 | lambed | |
| | 1 mg/kg | 55 | 48 | 12.0 | 0 | 0 | 0 | 0 | |
| | 1 ml/4 kg | 139 | 43 | 10.8 | 0 | 0 | 0 | 0 | |
| 16.0 | GROUP 2 (a) | 54 | 50 | 6.3 | 0 | 0 | 0 | 0 | 2 |
| | 2 mg/kg | 112 | 44 | 5.5 | 0 | 0 | 0 | 0 | 1 |
| | 1 ml/8 kg | 127 | 46 | 5.8 | 0 | 0 | 0 | 0 | 1 |
| 8.0 | GROUP 2 (b) | 53 | 44 | 11.0 | 0 | 0 | slaughtered (injury) | | |
| | 2 mg/kg | 88 | 48 | 12.0 | 0 | 0 | 0 | 1 | 3 |
| | 1 ml/4 kg | 146 | 43 | 10.8 | 0 | 0 | 0 | 0 | 2 |
| 20.0 | GROUP 3 (a) | 76 | 50 | 6.3 | 0 | 0 | | | |
| | 2.5 mg/kg | 126 | 44 | 5.5 | 0 | 0 | | | |
| | 1 ml/8 kg | 134 | 46 | 5.8 | 0 | 0 | | | |
| 10.0 | GROUP 3 (b) | 67 | 44 | 11.0 | 0 | 0 | | | |
| | 2.5 mg/kg | 75 | 42 | 10.5 | 0 | 0 | | | |
| | 1 ml/4 kg | 102 | 48 | 12.0 | 0 | 0 | | | |
| 24.0 | GROUP 4 (a) | 113 | 50 | 6.3 | 0 | 0 | | | |
| | 3 mg/kg | 131 | 44 | 5.5 | 0 | 0 | | | |
| | 1 ml/8 kg | 137 | 46 | 5.8 | 0 | 0 | | | |
| 12.0 | GROUP 4 (b) | 69 | 44 | 11.0 | 0 | 0 | | | |
| | 3 mg/kg | 84 | 42 | 10.5 | 0 | 0 | | | |
| | 1 ml/4 kg | 143 | 48 | 12.0 | 0 | 0 | | | |
| 32.0 | GROUP 5 (a) | 61 | 49 | 6.1 | 0 | 0 | | | |
| | 4 mg/kg | 141 | 44 | 5.5 | 0 | 0 | | | |
| | 1 ml/8 kg | 147 | 46 | 5.8 | 0 | 0 | | | |
| 16.0 | GROUP 5 (b) | 71 | 44 | 11.0 | 0 | 0 | | | |
| | 4 mg/kg | 110 | 42 | 10.5 | 0 | 0 | | | |
| | 1 ml/4 kg | 118 | 47 | 11.8 | 0 | 0 | | | |
| 40.0 | GROUP 6 (a) | 58 | 45 | 5.6 | 0 | 0 | | | |
| | 5 mg/kg | 68 | 49 | 6.1 | 0 | 0 | | | |
| | 1 ml/8 kg | 83 | 43 | 5.4 | 0 | 0 | | | |
| 20.00 | GROUP 6 (b) | 80 | 44 | 11.0 | 0 | 0 | | | |
| | 5 mg/kg | 124 | 47 | 11.8 | 0 | 0 | | | |
| | 1 ml/4 kg | 125 | 42 | 10.5 | 0 | 0 | | | |

*Figures shown in "week" columns are the number of lice seen in twenty wool partings.

TABLE 4

DGBE-Based Solvent*

| Deltamethrin (g/l) | Group | Sheep No. | Body-weight (kg) | Dose (ml) | Post-Treatment Inspections week 3 | week 6 | Challenge Inspections (Group 1 and Group 2) week 10 | week 12 | week 14 |
|---|---|---|---|---|---|---|---|---|---|
| 8.0 | GROUP 1 (c) | 60 | 45 | 5.6 | 0 | 0 | 0 | 1 | 1 |
| | 1 mg/kg | 73 | 49 | 6.1 | 0 | 0 | 0 | 3 | 0 |
| | 1 ml/8 kg | 85 | 43 | 5.4 | 0 | 0 | 0 | 1 | 1 |
| 4.0 | GROUP 1 (d) | 78 | 41 | 10.3 | <1/20 | 0 | 0 | 4 | 1 |
| | 1 mg/kg | 81 | 44 | 11.0 | 0 | 0 | 1 | 0 | 1 |
| | 1 ml/4 kg | 129 | 47 | 11.8 | 0 | 0 | 0 | 0 | 0 |
| 16.0 | GROUP 2 (c) | 62 | 45 | 5.6 | 0 | 0 | 0 | 3 | 2 |

TABLE 4-continued

DGBE-Based Solvent*

| Deltamethrin (g/l) | Group | Sheep No. | Body-weight (kg) | Dose (ml) | Post-Treatment Inspections week 3 | Post-Treatment Inspections week 6 | Challenge Inspections (Group 1 and Group 2) week 10 | Challenge Inspections (Group 1 and Group 2) week 12 | Challenge Inspections (Group 1 and Group 2) week 14 |
| --- | --- | --- | --- | --- | --- | --- | --- | --- | --- |
|  | 2 mg/kg | 74 | 49 | 6.1 | 0 | 0 | 0 | 1 | 1 |
|  | 1 ml/8 kg | 96 | 43 | 5.4 | 0 | 0 | slaughtered (injury) | | |
| 8.0 | GROUP 2 (d) | 18 | 41 | 10.3 | 0 | 0 | 0 | 1 | 0 |
|  | 2 mg/kg | 89 | 44 | 11.0 | 0 | 0 | 0 | 1 | 1 |
|  | 1 ml/4 kg | 132 | 47 | 11.8 | 0 | 0 | 0 | 1 | 2 |
| 20.0 | GROUP 3 (C) | 86 | 49 | 6.1 | <1/20 | 0 | | | |
|  | 2.5 mg/kg | 107 | 45 | 5.6 | 0 | 0 | | | |
|  | 1 ml/8 kg | 114 | 43 | 5.4 | 0 | 0 | | | |
| 10.0 | GROUP 3 (d) | 91 | 41 | 10.3 | 0 | 0 | | | |
|  | 2.5 mg/kg | 94 | 44 | 11.0 | 0 | 0 | | | |
|  | 1 ml/4 kg | 144 | 47 | 11.8 | 0 | 0 | | | |
| 24.0 | GROUP 4 (c) | 108 | 45 | 5.6 | 0 | 0 | | | |
|  | 3 mg/kg | 117 | 43 | 5.4 | 0 | 0 | | | |
|  | 1 ml/8 kg | 120 | 49 | 6.1 | 0 | 0 | | | |
| 12.0 | GROUP 4 (d) | 56 | 40 | 10.0 | 0 | 0 | | | |
|  | 3 mg/kg | 57 | 46 | 11.5 | 0 | 0 | | | |
|  | 1 ml/4 kg | 97 | 44 | 11.0 | 0 | 0 | | | |
| 32.0 | GROUP 5 (c) | 119 | 43 | 5.4 | 0 | 0 | | | |
|  | 4 mg/kg | 128 | 49 | 6.1 | 0 | 0 | | | |
|  | 1 ml/8 kg | 135 | 45 | 5.6 | 0 | 0 | | | |
| 16.0 | GROUP 5 (d) | 66 | 40 | 10.0 | 0 | 0 | | | |
|  | 4 mg/kg | 70 | 46 | 11.5 | 0 | 0 | | | |
|  | 1 ml/4 kg | 98 | 44 | 11.0 | 0 | 0 | | | |
| 40.0 | GROUP 6 (c) | 133 | 43 | 5.4 | 0 | 0 | | | |
|  | 5 mg/kg | 136 | 49 | 6.1 | 0 | 0 | | | |
|  | 1 ml/8 kg | 145 | 45 | 5.6 | 0 | 0 | | | |
| 20.0 | GROUP 6 (d) | 72 | 40 | 10.0 | 0 | 0 | | | |
|  | 5 mg/kg | 87 | 46 | 11.5 | 0 | 0 | | | |
|  | 1 ml/4 kg | 101 | 44 | 11.0 | 0 | 0 | | | |

*Figures shown in "week" columns are the number of lice seen in twenty wool partings.

TABLE 5

Results of Examinations of Shorn Untreated Control Group*
Untreated Controls

| Sheep No. | Body-weight (kg) | Week 3 | Week 6 |
| --- | --- | --- | --- |
| 65 | 51 | 10 | 10 |
| 77 | 56 | 9 | 8 |
| 79 | 52 | 17 | 15 |
| 82 | 38 | 24 | 31 |
| 95 | 54 | 18 | 29 |
| 104 | 28 | 37 | 35 |
| 105 | 52 | 20 | 8 |
| 111 | 29 | 24 | 23 |
| 116 | 44 | 10 | 16 |
| 122 | 39 | 22 | 18 |
| 123 | 36 | 19 | 18 |
| 130 | 35 | 18 | 17 |

*Figures show the number of lice seen in twenty wool partings.

Test 3 (varying solvent systems)

Table 6 gives the results for formulations of deltamethrin in a variety of other solvent systems when applied to recently sheared merino sheep.

TABLE 6

Various Solvent Systems

| Sheep No. | Body wt (kg) | Dose (ml) | Pre-Treatment | Week 4 | Week 6 | Week 8 | Formulations |
| --- | --- | --- | --- | --- | --- | --- | --- |
| 140 | 27 | 6 | 91 | 0 | 0 | 0 | 10 g/l deltamethrin in xylene system of Test 1 |
| 174 | 27 | 6 | 66 | 0 | 0 | 0 | |
| 175 | 26 | 6 | 30 | 1 | 0 | 0 | |
| 172 | 17 | 9 | 47 | 1 | 0 | 0 | 10 g/l deltamethrin |
| 178 | 33 | 8 | 90 | 0 | 0 | 0 | 2.5 g/l BHT |
| 180 | 34 | 8 | 47 | 0 | 0 | 0 | to 1 liter with cyclohexanone containing 50 ppm SUDAN RED IV |
| 131 | 25 | 6 | 51 | 0 | 0 | 0 | 10 g/l deltamethrin |
| 132 | 29 | 6 | 34 | 0 | 0 | 0 | 2.5 g/l BHT |
| 138 | 28 | 6 | 87 | 0 | 0 | 0 | 50 ppm SUDAN RED IV DGBE/cyclohexanone (65:35 w/w) to 1 liter |
| 142 | 32 | 8 | 73 | 0 | 0 | 0 | 10 g/l deltamethrin |
| 149 | 24 | 6 | 47 | 0 | 0 | 0 | 100 g/l mineral oil |
| 181 | 31 | 8 | 27 | 0 | 0 | 0 | 2.5 g/l BHT 50 ppm SUDAN RED IV cyclohexanone to 1 liter |
| 164 | 36 | 5 | 117 | 0 | 0 | 0 | 10 g/l deltamethrin |
| 165 | 33 | 8 | 47 | 0 | 0 | 0 | 100 g/l mineral oil |
| 177 | 30 | 4 | 27 | 0 | 0 | 0 | 2.5 g/l BHT |

TABLE 6-continued

Various Solvent Systems

| Sheep No. | Body wt (kg) | Dose (ml) | Pre-Treatment | Week 4 | Week 6 | Week 8 | Formulations |
|---|---|---|---|---|---|---|---|
| | | | | | | | 50 ppm SUDAN RED IV diethylene glycol mono-n-butyl ether (DGBE) to 1 liter |
| 143 | 31 | 8 | 90 | 1 | 0 | 0 | 10 g/l deltamethrin |
| 155 | 21 | 6 | 44 | 1 | 0 | 0 | 2.5 g/l BHT |
| 162 | 25 | 6 | 75 | 1 | 0 | 0 | 50 ppm SUDAN RED IV dipropylene glycol monomethyl ether (DPM) to 1 liter |
| 137 | 29 | 6 | 60 | 0 | 0 | 0 | 10 g/l deltamethrin |
| 163 | 28 | 6 | 72 | 0 | 0 | 0 | 2.5 g/l BHT |
| 169 | 21 | 6 | 39 | 0 | 0 | 0 | 100 g/l acetylated lanoline alcohols cyclohexanone to 1 liter |
| 156 | 23 | 6 | 57 | 1 | 0 | 0 | as for Example No. 10 |
| 176 | 31 | 8 | 180 | 2 | 0 | 0 | |
| 129 | 29 | — | 14 | 14 | 8 | 17 | Controls |
| 130 | 23 | — | 18 | 28 | 14 | 22 | |
| 154 | 25 | — | — | 171 | 47 | 72 | |
| 160 | 36 | — | 17 | 8 | 8 | 24 | |
| 171 | 30 | — | 17 | 29 | 24 | 20 | |

Test 4 (Varying Pyrethroids)

The efficacy of a variety of different pyrethroids applied as liquid pour-on formulations to merino sheep was determined. The results are given in Table 7. A backline application was made within 24 hours of shearing. All formulations used the xylene-based solvent system given in Test 1, except flumethrin which was formulated as a miscible oil formulation but which was diluted with the xylene-based solvent to achieve the lower concentrations.

The results show all the pyrethroids tested to be effective, although at the dosages used phenothrin and flumethrin did not give complete eradication.

Test 5 (Effect of Deltamethrin Against Keds)

The efficacy of deltamethrin against infestations of merino sheep with keds (Melophagus ovinus) was determined by applying 8 ml of deltamethrin in the xylene-based solvent system given in Test 1 as a backline treatment to twenty newly shorn sheep. Twenty further sheep were treated in the same way with deltamethrin in the DGBE-based solvent system given in Test 2. The concentration of deltamethrin was 10 g/l.

All forty sheep were re-examined 10 weeks after treatment and no live keds were found.

TABLE 7

Control of the Sheep-Biting Louse by a Number of Pyrethroids

| Compound/Dose/Formulation | Sheep No. | Result (No. of Lice) |
|---|---|---|
| CYPERMETHRIN | | |
| 5 mg/kg | 782 | 0 |
| (1 ml/5 kg-25 g/l formulation) | 767 | 7 |
| | 732 | 26 |
| 50 mg/kg | 756 | 0 |
| (1 ml/5 kg-250 g/l formulation) | 746 | 0 |
| | 733 | 0 (14/10 - D) |
| PHENOTHRIN | | |
| 25 mg/kg | 721 | 8 |
| (1 ml/5 kg-125 g/l formulation) | 765 | 23 |
| | 727 | 3 |
| 400 mg/kg | 724 | 8 |
| (4 ml/5 kg-500 g/l formulation) | 779 | 6 |
| | 753 | 18 |
| FENVALERATE | | |
| 10 mg/kg | 744 | 9 |
| (1 ml/5 kg-50 g/l formulation) | 740 | 3 |
| | 769 | 2 (14/10 - D) |

TABLE 7-continued

Control of the Sheep-Biting Louse by a Number of Pyrethroids

| Compound/Dose/Formulation | Sheep No. | Result (No. of Lice) |
|---|---|---|
| 100 mg/kg | 766 | 0 |
| (2 ml/5 kg-250 g/l formulation) | 770 | 0 |
| | 730 | 0 |
| FLUMETHRIN | | |
| 0.5 mg/kg | 783 | 21 |
| (1 ml/5 kg-2.5 g/l formulation) | 725 | 10 |
| | 719 | 1 |
| 12-16 mg/kg | 722 | 0 |
| (25 ml/30-40 kg-20 g/l formulation) | 755 | 5 |
| | 748 | 7 |
| CONTROLS | | |
| no treatment | 741 | 64 |
| | 737 | 52 |
| | 764 | 83 |
| | 754 | 53 |
| | 758 | 121 |
| | 723 | 55 |

D = died between 14/10 and 21/10

Test 6 (Time to Take Effect)

The time for the pyrethroid to fully clear the merino sheep following backline application of the liquid formulation was investigated and the results are shown in Table 8. These demonstrate that the pyrethroid takes a finite period to completely clear the sheep of lice. However, the sheep are substantially cleared within 15 days. The effect is also demonstrated in certain of the preceding Tables.

TABLE 8

Process of Reduction in Lice Numbers Following Pyrethroid Backline Treatment

| Group | Sheep No. | Lice Score Day | | | | | |
|---|---|---|---|---|---|---|---|
| | | 0 | 7 | 9 | 15 | 35 | 42 |
| Cypermethrin | 756 | >20 | 7 | 3 | 0 | 21 | 0 |
| 50 mg/kg | 746 | >20 | 7 | 2 | 5 | 21 | 0 |
| | 733 | >20 | 9 | 3 | 0 | 0 | 0 |
| Fenvalerate | 766 | >20 | 2 | 2 | 3 | 0 | 0 |
| 100 mg/kg | 770 | >20 | 6 | 1 | 0 | 0 | 0 |
| | 730 | >20 | 2 | 2 | 2 | 1I | 0 |
| Flumethrin | 722 | >20 | 10 | — | 8 | 4I | 0 |
| 12-16 mg/kg | 755 | >20 | 19 | — | 10 | 18I | 3I, 2A |
| | 748 | >20 | 12 | — | 4 | 7I, 2A | 4I, 3A |
| Controls | 741 | >20 | — | — | 14 | — | 64 (18) |
| | 737 | >20 | — | — | 15 | — | 52 (18) |

TABLE 8-continued

Process of Reduction in Lice Numbers
Following Pyrethroid Backline Treatment

| Group | Sheep No. | Lice Score Day | | | | |
|---|---|---|---|---|---|---|
| | | 0 | 7 | 9 | 15 | 35 | 42 |
| | 764 | >20 | — | — | 16 | — | 83 (19) |
| | 754 | >20 | — | — | 10 | — | 53 (15) |
| | 758 | >20 | — | — | 22 | — | 121 (19) |
| | 723 | >20 | — | — | 20 | — | 55 (13) |

I = immature lice
A = adult lice

(III) FORMULATIONS FOR USE ACCORDING TO THE PRESENT INVENTION

Suitable formulations are presented in the following Examples. In general, a suitable solvent system contains 0 to 100% by weight xylene, 0 to 100% by weight cyclohexanone, and up to 20% by weight corn oil.

EXAMPLE 1

10.1 g of technical deltamethrin (989 g active per kg), was dissolved in a solvent consisting of:

| cyclohexanone | 50 ppm |
|---|---|
| Sudan Red IV (oil soluble dye) | | and the volume adjusted to one litre to give a solution containing 10 g/l deltamethrin.

EXAMPLE 2

51 g of technical deltamethrin (989 g active constituent per kg) was dissolved in a solvent blend containing:

| xylene | 55% by weight |
|---|---|
| cyclohexanone | 30% by weight |
| corn oil | 15% by weight |
| Sudan Red IV | 1000 ppm | and the volume adjusted to one litre with the same solvent blend to give a solution containing 50 g/l deltamethrin.

EXAMPLE 3

10.1 g of technicaldeltamethrin (989 g active per kg) was dissolved in a solvent blend, containing:

| xylene | 55% by weight |
|---|---|
| cyclohexanone | 30% by weight |
| corn oil | 15% by weight |
| Sudan Red IV | 50 ppm | and the volume adjusted to one litre with the same solvent blend, to give a solution containing 10 g/l deltamethrin.

EXAMPLE 4

51 g of technical deltamethrin (989 g active per kg) was dissolved in the same solvent blend given in Example 3 and the volume adjusted to give a solution containing 50 g/l deltamethrin.

EXAMPLE 5

10.1 g of technical deltamethrin (989 g active per kg) was dissolved in a solvent consisting of:

| diethylene glycol monobutyl ether | 2500 ppm |
|---|---|
| BHT antioxidant | |
| Sudan Red IV | 50 ppm | and the volume adjusted to one litre with the same solvent to give a solution containing 10 g/l deltamethrin.

EXAMPLE 6

10.1 g of technical deltamethrin (989 g active per kg) ws dissolved in a solvent blend containing:

| cyclohexanone | 50% by weight |
|---|---|
| diethylene glycol monobutyl ether | 50% by weight |
| BHT antioxidant | 2500 ppm |
| Solvent Blue No. 36 | 50 ppm | and the volume adjusted with the same solvent blend to give a solution containing 10 g/l deltamethrin.

EXAMPLE 7

10.1 g of technical deltamethrin (989 g active per kg) was dissolved in a variety of solvent blends containing:

| diethylene glycol monobutyl ether or ethylene glycol monobutyl ether acetate | 85-90% by weight |
|---|---|
| isopropyl myristate | 10-15% by weight |
| BHT antioxidant | 2500 ppm |
| Sudan Red IV | 50 ppm | and the volume adjusted with the respective solvent blend to give a solution containing 10 g/l deltamethrin.

EXAMPLE 8

Amounts of 2.6, 10.5, 42.5 and 84.2 g of technical cypermethrin (950 g active per kg) were dissolved in a solvent blend containing:

| xylene | 55% by weight |
|---|---|
| cyclohexanone | 30% by weight |
| corn oil | 15% by weight | and the volume adjusted to one litre with the same solvent blend to give solutions containing 2.5 g, 10 g, 40 g and 80 g per litre respectively of cypermethrin.

EXAMPLE 9

103 g of technical permethrin (970 g active per kg) in which the cis:trans isomer (arising from the two asymmetric carbon atoms in the cyclopropane ring) ratio was 25:75 was dissolved in a solvent blend containing:

| xylene | 55% by weight |
|---|---|
| cyclohexanone | 30% by weight |
| corn oil | 15% by weight | and the volume adjusted to one litre with the same solvent blend to give a solution containing 100 g/l permethrin.

EXAMPLE 10

An aqueous suspension of deltamethrin was prepared by suspending 10.1 g of technical deltamethrin of average particle size 2 to 5 microns in an aqueous formulation containing:

| | |
|---|---|
| non-ionic wetting agent | 1.5 g |
| {1 mole nonylphenol condensed with 15 moles of ethylene oxide} | |
| fumed silicon dioxide | 5.0 g |
| xantham gum | 4.0 g |
| propylene glycol | 60.0 g |
| formaldehyde | 1.0 g |
| silicone oil (antifoaming agent) | 1.0 g |
| water | to one liter. |

Various otherdeltamethrin suspensions in the range 1 to 500 g/l deltamethrin were also prepared.

The claims defining the invention are as follows:

1. A method of treating a sheep having lice or a ked infestation, which comprises applying to said sheep a 2 ml to 15 ml volumn of a liquid pour-on formulation containing an effective lice or ked infestation treatment amount of deltamethrin in a lower alkyl ether of a glycol.

2. A method of treating a sheep having a lice or ked infestation, which comprises applying to said sheep a 2 ml to 15 ml volumn of a liquid pour-on formulation containing an effective lice or ked infestation treatment amount of permethrin, phenothrin, cypermethrin, cyhalothrin, flumethrin, cyfluthrin, cyphenothrin, tralomethrin, tralocythrin or fenvalerate in a lower alkyl ether of a glycol.

3. A topical liquid formulation for treating lice or ked infection comprising deltamethrin in a lower alkyl ether of a glycol, said formulation containing 1 to 250 mg/ml of deltamethrin.

4. A topical liquid formulation for treating lice or ked infections comprising the active ingredient permethrin, phenothrin, cypermethrin, cyhalothrin, flumethrin, cyfluthrin, cyphenothrin, tralomethrin, tralocythrin or fenvalerate in a lower alkyl ether of glycol, said formulation containing 1 to 250 mg/ml of the active ingredient.

* * * * *